US012751913B2

(12) United States Patent
Roumeliotis et al.

(10) Patent No.: US 12,751,913 B2
(45) Date of Patent: Oct. 6, 2026

(54) COSMETIC PRODUCT ENRICHED WITH BIOACTIVE COMPONENTS OF PROPOLIS WITH DIRECT EXTRACTION FROM BEESWAX SPRAYED WITH PROPOLIS TINCTURE AND METHOD OF PRODUCTION THEREOF

(71) Applicant: Nikolaos Roumeliotis, Athens (GR)

(72) Inventors: Nikolaos Roumeliotis, Athens (GR); Ioannis Mourtzinos, Salonika (GR); Athanasia Vasilaki, Salonika (GR); Aikaterini Vasilatou, Nea Smirni Attikis (GR); Vasileios Roumeliotis, Tripoli (GR); Konstantina Anagnou, Tripoli (GR)

(73) Assignee: Roumeliotis Nikolaos, Athens (GR)

( * ) Notice: Subject to any disclaimer, the term of this patent is extended or adjusted under 35 U.S.C. 154(b) by 1050 days.

(21) Appl. No.: 17/623,387

(22) PCT Filed: Jun. 28, 2019

(86) PCT No.: PCT/GR2019/000045

§ 371 (c)(1),
(2) Date: Dec. 28, 2021

(87) PCT Pub. No.: WO2020/260911

PCT Pub. Date: Dec. 30, 2020

(65) Prior Publication Data

US 2022/0370341 A1 Nov. 24, 2022

(51) Int. Cl.

*A61K 8/98* (2006.01)
*A61K 8/92* (2006.01)
*A61Q 5/02* (2006.01)
*A61Q 19/10* (2006.01)

(52) U.S. Cl.

CPC .............. *A61K 8/988* (2013.01); *A61K 8/927* (2013.01); *A61Q 5/02* (2013.01); *A61Q 19/10* (2013.01)

(58) Field of Classification Search

None

See application file for complete search history.

(56) References Cited

U.S. PATENT DOCUMENTS

2016/0038611 A1 2/2016 Vile et al.

FOREIGN PATENT DOCUMENTS

| | | | |
|---|---|---|---|
| DE | 3533864 | A1 | 4/1986 |
| EP | 0976399 | A1 | 2/2000 |
| RO | 126992 | A2 * | 1/2012 |
| RU | 82548 | U1 * | 5/2009 |
| WO | 2014186851 | A1 | 11/2014 |

OTHER PUBLICATIONS

English translation of RU-82548-U1 (Year: 2009).*
English translation of RO-126992-A2 (Year: 2012).*
English Translation of WO 2014/186851 A1 (Year: 2014).*
International Search Report and Written Opinion issued in corresponding International Application No. PCT/GR2019/000045, mailed Feb. 24, 2020, pp. 1-15, European Patent Office, Rijswijk, Netherlands.

* cited by examiner

*Primary Examiner* — Nicole P Babson

(74) *Attorney, Agent, or Firm* — HAUPTMAN HAM, LLP

(57) ABSTRACT

Cosmetic products with a high concentration of propolis bioactive components produced using a new method that achieves increased concentration of, beneficial for skin health, phenolic components. The increase in the concentration of bioactive components is achieved by incorporating a piece of beeswax of specific dimensions into the cosmetic product after having been sprayed with propolis tincture. In the cosmetic product the extraction of the bioactive components of the propolis (terpenes, phenolic components) takes place assisted by the surfactants of the cosmetic product.

9 Claims, No Drawings

COSMETIC PRODUCT ENRICHED WITH BIOACTIVE COMPONENTS OF PROPOLIS WITH DIRECT EXTRACTION FROM BEESWAX SPRAYED WITH PROPOLIS TINCTURE AND METHOD OF PRODUCTION THEREOF

RELATED APPLICATION

The present application is a National Phase of International Application Number PCT/GR2019/000045, filed Jun. 28, 2019.

TECHNOLOGICAL FIELD

The present invention relates to a cosmetic product enriched with bioactive components of propolis and to a method of extracting bioactive components of propolis in cosmetic products by immersing and extracting apiculture products (propolis and beeswax) in the cosmetic product. In particular, a piece of beeswax of specific dimensions is incorporated into the cosmetic product after having been sprayed with propolis tincture. The extraction of the propolis bioactive components (terpenes, phenolic components) takes place in the cosmetic product assisted by the surfactants of the cosmetic product.

TECHNICAL BACKGROUND

Until now, no such product has been known to have been produced using this particular method.

In particular, propolis is one of the apiculture products whose ingredients are used in cosmetic products and dietary supplements due to their beneficial, to the health, properties. It is a sticky and resinous mixture resulting from the mixing of plant secretions collected from bees (*Apis mellifera* L.) which is mixed with pollen and enzymes. The composition of propolis depends mainly on its geographical and botanical origins, on the collection season and climatic conditions. In general, it consists of 50% resins, 30% waxes, 5% pollen and 10% essential oils. Its beneficial properties are due to its bioactive components, which are mainly phenolic acids, flavonoids, terpenoids and their derivatives.

The main beneficial effects of propolis are anti-inflammatory and reconstructive, while the photo-protection that it can also provide to the skin is important. The application of propolis products induces skin detoxification and the extinction of free radicals which is a result of ultraviolet radiation, while at the same time it regulates collagen production and antiaging mechanisms (Saewan et al, 2015, Olczyk et al, 2013, Kim & Yoo, 2016). At the same time, its antimicrobial properties, which help maintain tissue homeostasis and are due to phenolic and terpenoid components, are also important. For all these reasons, propolis is considered to be by many researchers among the possible ingredients of pharmaceutical cosmetics, with an effect against radiation, aging, inflammation and against micro-organisms, and also as a means of preventing skin homeostasis.

Propolis is generally incorporated into products in the form of propolis extracts, with most common the propolis tincture (ethanolic extract). During the last years, extraction solvents which are more environmentally friendly, such as glycols (butylene glycol, propylene glycol, glycerol) and water have been used as extractors. The extraction process involves maceration of the propolis in the solvent and then filtering in order to remove the insoluble propolis. The extraction process may include heating and/or energy transfer using techniques such as microwaves or ultrasounds. When aiming at the production of the final extract in solid powder form, then the drying stage is carried out either by spray-drying or by freeze-drying.

A major disadvantage of extractions production is that it involves many stages such as maceration with or without the use of energy, filtration as well as drying when we wish to produce the extract in the form of solid powder. All these methods include energy-consuming processes and the use of chemical additives such as maltodextrins in the case of spray-drying. All the above considerably increase the cost of the production process while burdening both the environment and the product itself.

All the above disadvantages have prompted us to find a solution, the result of which is the object of the present invention. With our invention the above disadvantages are eliminated. Because no prior treatment of the sample or the use of special pharmaceutical processes is required in order to obtain the bioactive components of propolis. The addition of the wax-propolis system to a cosmetic product is sufficient to enrich the product, since the product includes surfactants which promote the transfer of phenolic and terpene components. In this way, the use of chemical processes is avoided. Furthermore, the avoidance of the use of organic solvents, and energy in any form, makes the production method of the invented products environmentally friendly and ecological. In addition, the invented method is the simplest method of enriching cosmetics with natural components of the hive, where there is no use of high temperatures, ultrasounds or microwaves, methods that require energy consumption and vertically increase the production costs, while the final product has specific specifications regarding the total polyphenols and the antioxidant capacity.

Finally, the process of transferring bioactive components of propolis from the piece of beeswax to the cosmetic product is an active process that takes place throughout the life of the cosmetic product within its packaging and the proposed method does not affect the pH of the product which is a critical physicochemical parameter of a cosmetic.

The confirmation of the transfer of bioactive components of propolis to the cosmetic system is made by measuring the antioxidant capacity in terms of radical scavenging.

Therefore, the basic purpose of the present invention is the production of cosmetic products, such as shower gel and shampoo, with a high concentration of bioactive components of propolis obtained by incorporating wax sprayed with propolis tincture into each packaging of the cosmetic product. In this way, throughout the life of the cosmetic product, bioactive components of propolis are transferred from the surface of the wax to the mass of the cosmetic product.

DISCLOSURE OF THE INVENTION

In order to make our invention understood by those skilled in the art, the method of enriching a cosmetic product with active components of propolis by directly extracting them from beeswax sprayed with propolis tincture and incorporated into the mass of the cosmetic product is described below.

The process begins with the treatment of the beeswax. At the first stage, the production of high quality and purity of wax is ensured by placing it in a special proving oven of constant temperature ranging from 60 to 70 degrees Celsius. Then in the second stage of the process, the melted wax is collected and washed with running water in order to be washed from honey residues. In the third stage of the process, the wax is repositioned in warm water in order to remove any debris (parts of stones, sticks, leaves, cocoons, etc.). In the fourth stage of the process, the wax which has already been cleared is collected, re-melted and placed in a manually-operated machine in order to prepare the wax sheets which are cut into a 5 cm×0.8 cm dimension or into any other desired dimension and then, in the fifth stage of the process, they are sprayed with propolis tincture, which has been produced by blending biological propolis with ethanol (96°) in a proportion of 1:1. Then, in the sixth stage of the process, the wax is allowed to dry for at least 8 hours at room temperature (15-25° C.) in order for the ethanol to be evaporated and alcohol-free product to be produced. In the final stage, the piece of wax which has received the above treatment is incorporated into the cosmetic product (shampoo, shower gel) in a specific proportion: 1 piece of wax (5 cm×0.8 cm) in 40 mL of product.

In this way, the antioxidant capacity of the products is increased due to the transfer of bioactive components of propolis, eventually aiming at their transfer to the skin. The beneficial ingredients of propolis protect the skin from negative environmental factors The confirmation of transfer of phenolic components is made by measuring the antioxidant capacity which is achieved by measuring the radical scaveging of 2,2-diphenyl-1-picrylhydrazyl (DPPH) radical and the values are compared with the values of the measurements of ethanol and water mass where the beeswax is added. Measurements take place over a period of fifteen days after the preparation of the solutions.

| PRODUCT/EXTRACTING AGENT | DPPH radical scaveging (mMTRE) |
|---|---|
| Water | 0.1 |
| Ethanol | 0.4 |
| Shower gel (5-10% surfactants content) | 0.4 |
| Shampoo (10-15% surfactants content) | 0.7 |

The following examples are given in order to explain the present invention:

EXAMPLE 1

Beeswax of specific dimensions sprayed with propolis tincture is incorporated into a shower gel in a proportion of: 1 piece of honeycomb per 40 mL of shower gel. After 20 days, the antioxidant capacity is measured The value of antioxidant capacity is shown in Table 1.

TABLE 1

| Parameter | Value |
|---|---|
| Antioxidant capacity | >0.4 (Trolox equivalent) |

EXAMPLE 2

Beeswax of specific dimensions sprayed with propolis tincture is incorporated into a shampoo in a ratio of: 1 piece of honeycomb per 40 mL of shower gel. After 20 days, the antioxidant capacity is measured.

The value of antioxidant capacity is shown in Table 2.

TABLE 2

| Parameter | Value |
|---|---|
| Antioxidant capacity | >0.7 (Trolox equivalent) |

The invention claimed is:

1. A method of producing a cosmetic product enriched with bioactive components of propolis, comprising:

(a) forming a solid beeswax element having a defined shape and dimensions;

(b) applying a propolis-containing liquid composition onto a surface of the solid beeswax element to form a surface-treated beeswax element;

(c) drying the surface-treated beeswax element to remove solvent and immobilize propolis components on the surface of the solid beeswax element, thereby forming a dried, propolis-treated solid insert; and (d) inserting the dried, propolis-treated solid insert into a container containing a cosmetic formulation, wherein the cosmetic formulation comprises surfactants, wherein the bioactive components of propolis are transferred from a surface of the dried, propolis-treated solid insert to the cosmetic formulation throughout a life of the cosmetic product, assisted by the surfactants of the cosmetic formulation.

2. The method according to claim 1, wherein forming the solid beeswax element comprises heating beeswax at a temperature of 60° C. to 70° C. to obtain melted beeswax.

3. The method according to claim 2, further comprising cleaning the melted beeswax by washing to remove residual honey and solid impurities prior to forming the solid beeswax element.

4. The method according to claim 3, wherein forming the solid beeswax element comprises re-melting the cleaned beeswax and shaping the beeswax using a molding apparatus to form wax sheets.

5. The method according to claim 4, wherein applying the propolis-containing liquid composition comprises spraying a propolis tincture prepared by blending propolis with ethanol having a concentration of 96 percent onto a surface of each of the wax sheets, thereby forming surface-treated wax sheets.

6. The method according to claim 5, wherein drying the surface-treated wax sheets comprises maintaining the wax sheets at room temperature for at least 8 hours to evaporate ethanol and obtain alcohol-free wax sheets containing surface-bound propolis components.

7. The method according to claim 1, wherein the dried, propolis-treated solid insert has dimensions of approximately 5 centimeters by 0.8 centimeters and is inserted into the container in a proportion of one dried, propolis-treated solid insert per 40 milliliters of the cosmetic formulation.

8. The method according to claim 1, further comprising confirming transfer of the bioactive components of propolis into the cosmetic formulation by measuring antioxidant capacity of the cosmetic formulation.

9. The method according to claim 1, wherein the surfactants are present in a concentration of 5 to 15 percent.

* * * * *